United States Patent
Gavardinas et al.

(10) Patent No.: US 12,428,377 B2
(45) Date of Patent: Sep. 30, 2025

(54) SODIUM-HYDROGEN EXCHANGER 3 INHIBITOR COMPOUNDS

(71) Applicant: Eli Lilly and Company, Indianapolis, IN (US)

(72) Inventors: Kostas Gavardinas, Carmel, IN (US); Prabhakar Jadhav, Chantilly, VA (US); Xiaojun Wang, Carmel, IN (US); John Rowley Wetterau, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 951 days.

(21) Appl. No.: 17/611,456

(22) PCT Filed: May 8, 2020

(86) PCT No.: PCT/US2020/031999
§ 371 (c)(1),
(2) Date: Nov. 15, 2021

(87) PCT Pub. No.: WO2020/231770
PCT Pub. Date: Nov. 19, 2020

(65) Prior Publication Data
US 2022/0213042 A1    Jul. 7, 2022

Related U.S. Application Data

(60) Provisional application No. 62/848,652, filed on May 16, 2019.

(51) Int. Cl.
| | |
|---|---|
| *C07D 217/14* | (2006.01) |
| *A61K 31/4725* | (2006.01) |
| *A61K 31/496* | (2006.01) |
| *A61P 9/12* | (2006.01) |
| *C07D 409/12* | (2006.01) |

(52) U.S. Cl.
CPC ........ *C07D 217/14* (2013.01); *A61K 31/4725* (2013.01); *A61K 31/496* (2013.01); *A61P 9/12* (2018.01); *C07D 409/12* (2013.01)

(58) Field of Classification Search
CPC .................................................. C07D 217/14
See application file for complete search history.

(56) References Cited

FOREIGN PATENT DOCUMENTS

| | | |
|---|---|---|
| WO | 2010/078449 A2 | 8/2010 |
| WO | 2014/169094 A2 | 10/2014 |
| WO | 2018/034883 A1 | 2/2018 |

OTHER PUBLICATIONS

International Search Report of PCT/US2020/031999 (filed May 8, 2020 by Eli Lilly and Company), mailed by the European Patent Office on Jul. 7, 2020.
Written Opinion of the International Searching Authority of PCT/US2020/031999 (filed May 8, 2020 by Eli Lilly and Company), mailed by the European Patent Office on Jul. 7, 2020.

*Primary Examiner* — Golam M Shameem
(74) *Attorney, Agent, or Firm* — Quarles & Brady LLP

(57) ABSTRACT

The present invention relates to sodium-hydrogen exchanger 3 (NHE3) inhibitor compounds of the Formula:

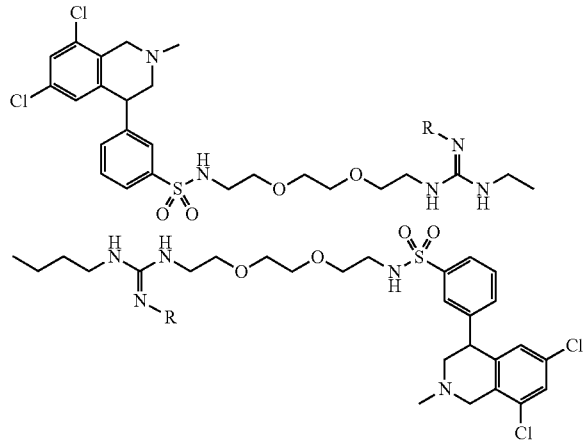

to pharmaceutical compositions comprising the compound and to the use of the compound for the treatment of certain diseases associated with elevated sodium and/or phosphate levels.

7 Claims, No Drawings

SODIUM-HYDROGEN EXCHANGER 3 INHIBITOR COMPOUNDS

The present invention relates to novel sodium-hydrogen exchanger 3 (NHE3) inhibitor compounds, to pharmaceutical compositions comprising the compounds and to the use of the compounds for the treatment of certain diseases associated with elevated sodium and/or phosphate levels. The present invention further relates to the use of novel NHE3 compounds in combination with certain sodium-dependent phosphate co-transporter (NPT2b) inhibitors.

NHE3 is an epithelial sodium-hydrogen exchanger present in the mammalian small intestine, colon, gall bladder, renal proximal tube and thick and thin limbs of the loop of Henle. In the intestine, NHE3 regulation occurs acutely as part of digestion and is inhibited in the immediate postprandial period. NHE3 null mice exhibit perturbed sodium-fluid balance, highlighting NHE3's role in preserving volume homeostasis and indicating that NHE3 is the major contributor to intestinal sodium uptake. In addition, recent in vivo studies have shown that NHE3 inhibition causes a decrease in intestinal phosphate absorption (Orlowski, J., et al., *Pflugers Arch.—Eur. J. Physiol.*, 2004, 447:549-565, King, A. J., et al., *Sci. Transl. Med.*, 2018, 10, 1-17).

Excessive consumption of sodium, which is ubiquitous in western diets, is strongly associated with the manifestation of hypertension, which is in turn associated with increased risk of cardiovascular and kidney disease. Maintaining an optimal level of sodium intake can help manage blood pressure and prevent cardiovascular and kidney disease (Weintraub, W. S., et al., *J. Am. Coll. Cardiol.*, 2015, 65 (10), 1042-1050).

Reduced renal clearance in chronic kidney disease (CKD) and end-stage renal disease (ESRD) leads to increases phosphate burden, which can promote renal secondary hyperparathyroidism and eventually result in hyperphosphatemia (Wolf M., *J. Am. Soc. Nephrol.*, 2010, 21, 1427-1435). CKD is not only the most common cause of hyperphosphatemia in humans, but also in adult cats and dogs (Kidder, A., et al, *J. Feline Med. Sur.*, 2009, 11, 913-924). A well-documented consequence of hyperphosphatemia is cardiovascular disease (CVD), which can manifest as vascular and heart valve calcification, left ventricular hypertrophy, heart failure, arrhythmia and sudden cardiac death (Fujii, H., et al., *Clin. Exp. Nephrol.*, 2017, 21(S1), S53-S63). Secondary hyperparathyroidism resulting from the increased phosphate burden can also lead to bone disease (Yuen, N. K., et al., *Perm. J.*, 2016, 20(3), 15-127).

Effectively decreasing intestinal phosphate absorption through dietary phosphate restriction and use of an inhibitor of phosphate absorption will decrease the phosphate burden in CKD and help decrease the sequelae contributing to CVD, bone disease and a further deterioration of renal function.

WO2010/078449 discloses compounds and methods for inhibiting NHE-mediated antiport in the treatment of disorders associated with fluid retention or salt overload and gastrointestinal tract disorders. WO2014/169094 discloses NHE3-binding compounds and methods for inhibiting phosphate transport.

In view of the foregoing, it is recognised that excessive sodium and phosphate absorption in the intestine contribute to an increased incidence of diseases such as hypertension, CKD, CVD, bone disease and related mortality. Accordingly, there is a need for alternative treatments for these conditions, in particular for treatments that inhibit NHE3. In particular, there is a need for compounds which are effective at reducing sodium and phosphate absorption in vivo while possessing a high degree of selectivity for NHE3 inhibition. It is furthermore desirable to have NHE3 inhibitor compounds which are effective in combination with NPT2b inhibitor compounds.

Accordingly, the present invention provides a compound of Formula I:

Formula I

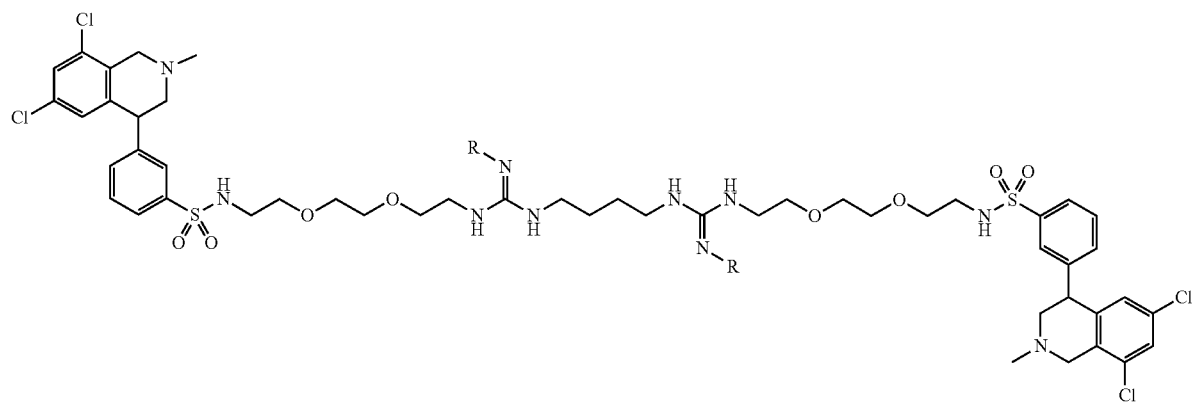

wherein both R are CN or both R are $C(O)NH_2$, or a pharmaceutically acceptable salt thereof.

In a particular embodiment, both R are $C(O)NH_2$.

In a particular embodiment, the compound is a compound of the formula:

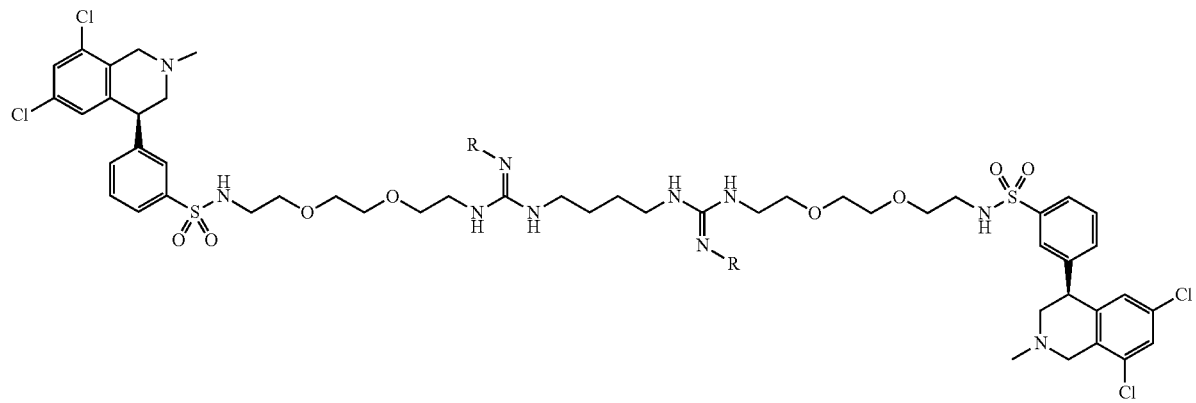
or a pharmaceutically acceptable salt thereof.
In a further embodiment, the compound is a compound of the formula:
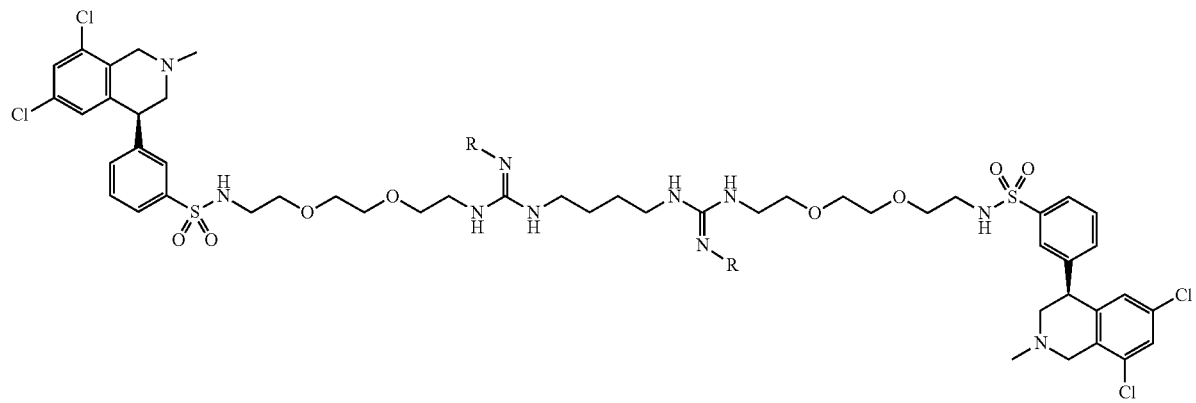
In a further embodiment, the compound is the dihydrochloride salt of:
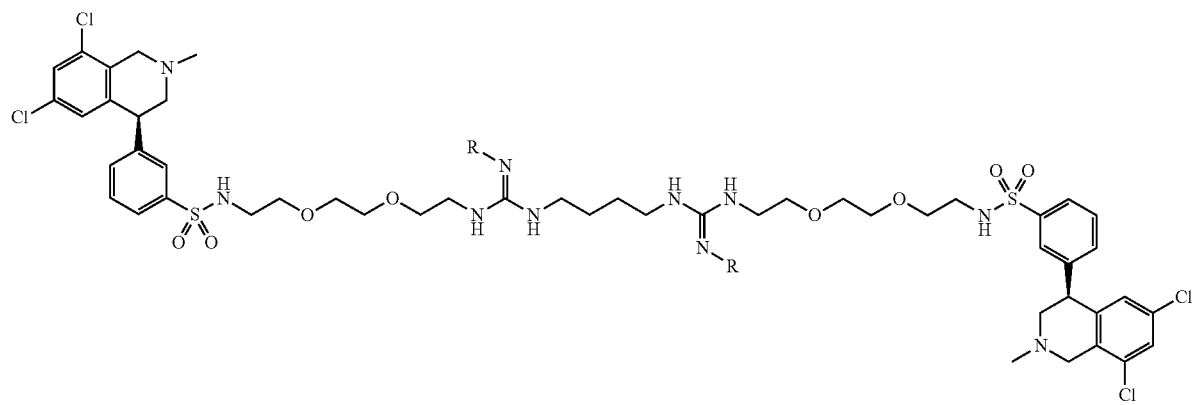
In a particular embodiment, the compound is a compound of the formula:

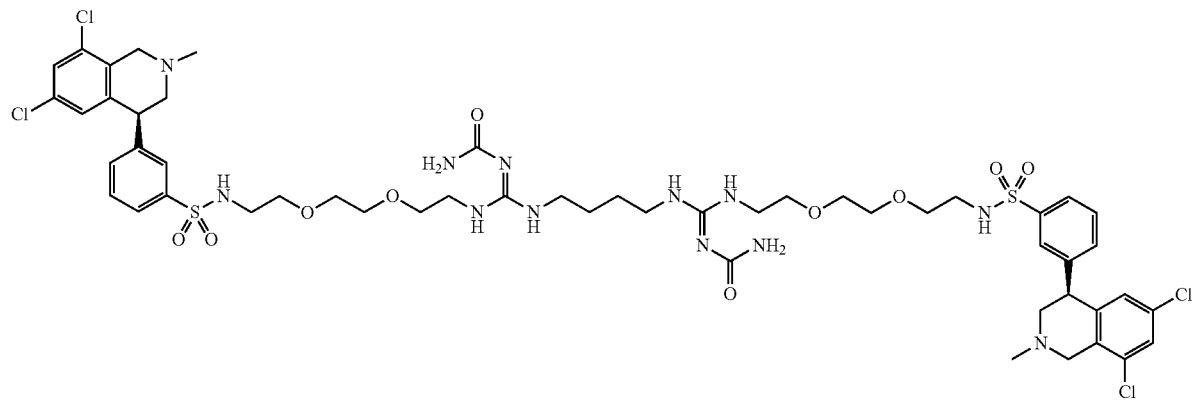 [SMILES: CN1Cc2c(Cl)cc(Cl)cc2[C@H](c2cccc(S(=O)(=O)NCCOCCOCCN/C(=N\C(N)=O)NCCCCN/C(=N/C(N)=O)NCCOCCOCCNS(=O)(=O)c3cccc([C@@H]4CN(C)Cc5c(Cl)cc(Cl)cc54)c3)c2)C1]

In a particular embodiment, the compound is the dihydrochloride salt of:

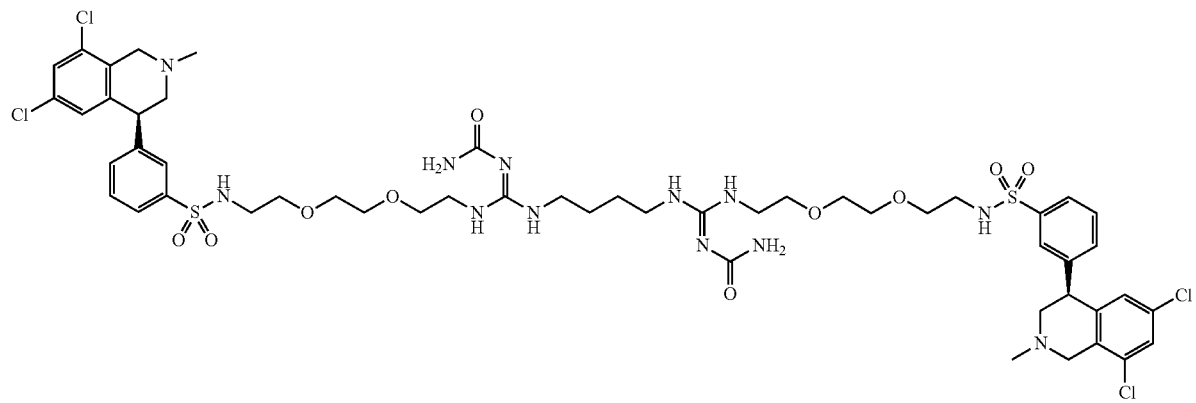 [SMILES: CN1Cc2c(Cl)cc(Cl)cc2[C@H](c2cccc(S(=O)(=O)NCCOCCOCCN/C(=N\C(N)=O)NCCCCN/C(=N/C(N)=O)NCCOCCOCCNS(=O)(=O)c3cccc([C@@H]4CN(C)Cc5c(Cl)cc(Cl)cc54)c3)c2)C1]

The present invention also provides a method of treating a disease selected from the group consisting of CKD, hyperphosphatemia, secondary hyperparathyroidism, heart failure, hypertension and CVD comprising administering to a mammal in need thereof a therapeutically effective amount of a compound of Formula I, or a pharmaceutically acceptable salt thereof. In an embodiment, the invention provides a method of treating CKD in cats comprising administering to a cat in need thereof a therapeutically effective amount of a compound of Formula I, or a pharmaceutically acceptable salt thereof.

The present invention also provides a method of treating a disease selected from the group consisting of CKD, hyperphosphatemia, secondary hyperparathyroidism, heart failure, and CVD comprising administering to a mammal in need thereof a therapeutically effective combination of a compound of Formula I, or pharmaceutically acceptable salt thereof, in combination with a compound of Formula II:

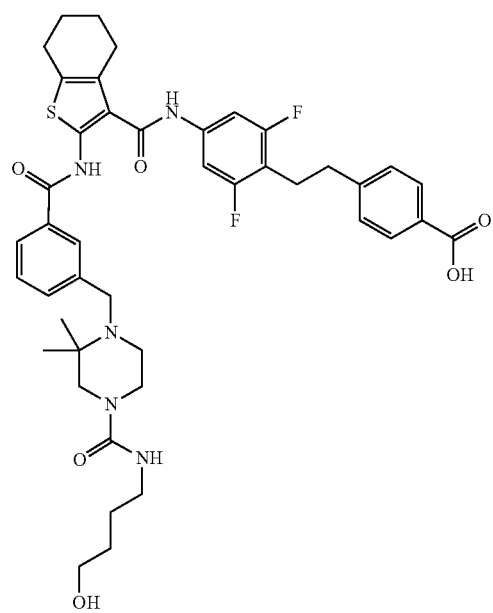

Formula II or a pharmaceutically acceptable salt thereof. In an embodiment, the invention provides a method of treating CKD in cats comprising administering to a cat in need thereof a therapeutically effective combination of a compound of Formula I, or a pharmaceutically acceptable salt thereof, in combination with a compound of Formula II, or a pharmaceutically acceptable salt thereof.

Furthermore, this invention provides a compound of Formula I, or a pharmaceutically acceptable salt thereof, for use in therapy. In particular, the present invention provides a compound of Formula I, or a pharmaceutically acceptable salt thereof, for use in the treatment of CKD, hyperphosphatemia, secondary hyperparathyroidism, heart failure, hypertension or CVD. In an embodiment, the invention provides a compound of Formula I, or a pharmaceutically acceptable salt thereof, for use in the treatment of CKD in cats.

Furthermore, this invention provides a compound of Formula I, or a pharmaceutically acceptable salt thereof, for use in simultaneous, separate or sequential combination with a compound of Formula II, or a pharmaceutically acceptable salt thereof, in the treatment of CKD, hyperphosphatemia, secondary hyperparathyroidism, heart failure or CVD. In an embodiment, the invention provides a compound of Formula I, or a pharmaceutically acceptable salt thereof, for use in simultaneous, separate or sequential combination with a compound of Formula II, or a pharmaceutically acceptable salt thereof, in the treatment of CKD in cats.

Furthermore, this invention provides a compound of Formula II, or a pharmaceutically acceptable salt thereof, for use in simultaneous, separate or sequential combination with a compound of Formula I, or a pharmaceutically acceptable salt thereof, in the treatment of CKD, hyperphosphatemia, secondary hyperparathyroidism, heart failure or CVD. In an embodiment, the invention provides a compound of Formula II, or a pharmaceutically acceptable salt thereof, for use in simultaneous, separate or sequential combination with a compound of Formula I, or a pharmaceutically acceptable salt thereof, in the treatment of CKD in cats.

Furthermore, this invention provides a pharmaceutical composition comprising a compound of Formula I, or a pharmaceutically acceptable salt thereof, with a pharmaceutically acceptable excipient, carrier, or diluent.

Furthermore, this invention provides a pharmaceutical composition comprising a compound of Formula I, or a pharmaceutically acceptable salt thereof, with a pharmaceutically acceptable excipient, carrier, or diluent additionally comprising a compound of Formula II, or a pharmaceutically acceptable salt thereof.

Furthermore, the present invention provides the use of a compound of Formula I, or a pharmaceutically acceptable salt thereof, for the manufacture of a medicament for treating CKD, hyperphosphatemia, secondary hyperparathyroidism, heart failure, hypertension or CVD. In an embodiment, the invention provides a compound of Formula I, or a pharmaceutically acceptable salt thereof, for the manufacture of a medicament for treating CKD in cats.

The compounds and combinations of the present invention may be used in the treatment of diseases and conditions associated with sodium and/or phosphate imbalance including: hyperphosphatemia, in particular hyperphosphatemia in ESRD or CKD or familial hyperphosphatemia; hyperparathyroidism, in particular secondary hyperparathyroidism associated with CKD; calcium phosphate kidney stones; heart valve calcification associated with CKD or ESRD; bone fractures associated with CKD; calciphylaxis; tumoral calcinosis; and acute kidney disease.

In a particular embodiment, the compound of Formula II is the free acid. In a particular embodiment, the compound of Formula II is the disodium salt. The free acid compound of Formula II is herein referred to as "Compound A".

As used herein, the term "treating" or "to treat" includes restraining, slowing, stopping, or reversing the progression or severity of an existing symptom or disorder.

In an embodiment, the mammal to be treated is a human. In another embodiment, the mammal is a cat or dog, preferably a cat.

As used herein, the term "effective amount" refers to the amount or dose of compound of Formula I or II, or a pharmaceutically acceptable salt thereof which, upon single or multiple dose administration to the mammal, provides the desired effect in the patient under diagnosis or treatment.

An effective amount can be determined by one skilled in the art by the use of known techniques and by observing results obtained under analogous circumstances. In determining the effective amount for a patient, a number of factors are considered, including, but not limited to: the species of patient; its size, age, diet, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances. The compounds of Formula I and II are effective at a dosage per day that falls within the range of about 0.01 to about 15 mg/kg of body weight.

The compounds of Formula I or II are formulated as pharmaceutical compositions administered by any route which makes the compound bioavailable. Preferably, such compositions are for oral administration. Such pharmaceutical compositions and processes for preparing same are well known in the art (See, e.g., Remington, J. P., "*Remington: The Science and Practice of Pharmacy*", L. V. Allen, Editor, 22$^{nd}$ Edition, Pharmaceutical Press, 2012).

The compounds of Formula I and the pharmaceutically acceptable salts thereof may be used in the therapeutic uses of the invention, with certain configurations being preferred. The following list of compounds of the present invention describe such configurations. It will be understood that these preferences are applicable both to the therapeutic uses and to the compounds of the invention.

The skilled person will appreciate that for compounds in which both R are C(O)NH$_2$, the amidine urea moiety may exist in either the E or Z configuration and may readily switch between the two. The compounds of the present invention include both the E and Z isomers, as well as mixtures thereof.

Compounds of Formula I include:
Formula Ia′
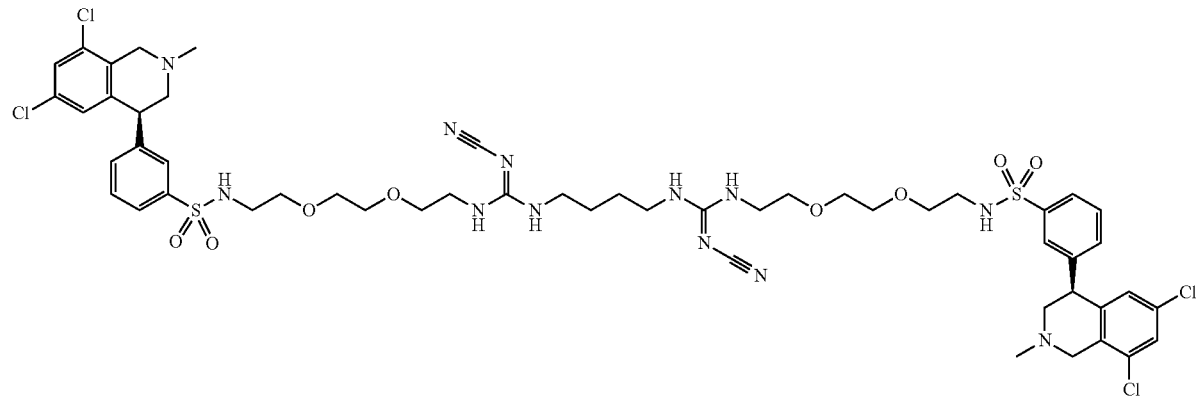
Formula Ia″
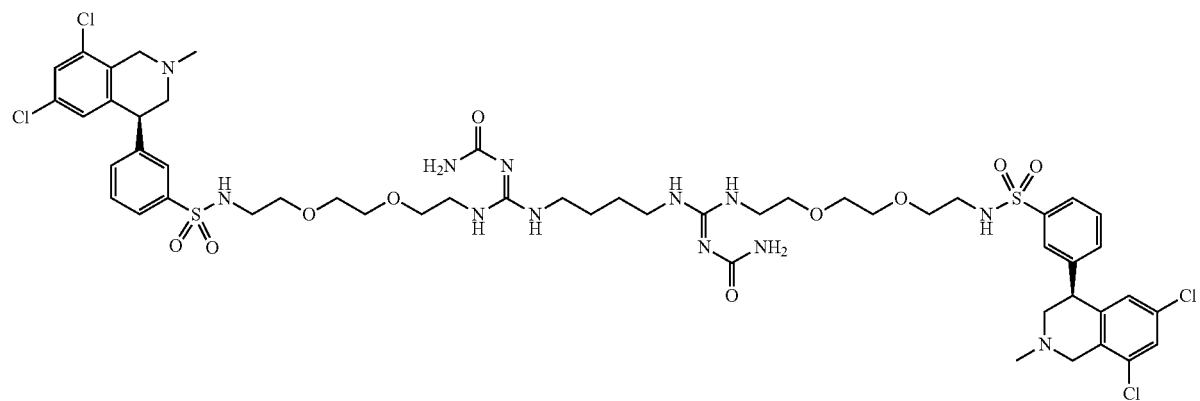
Formula Ib′
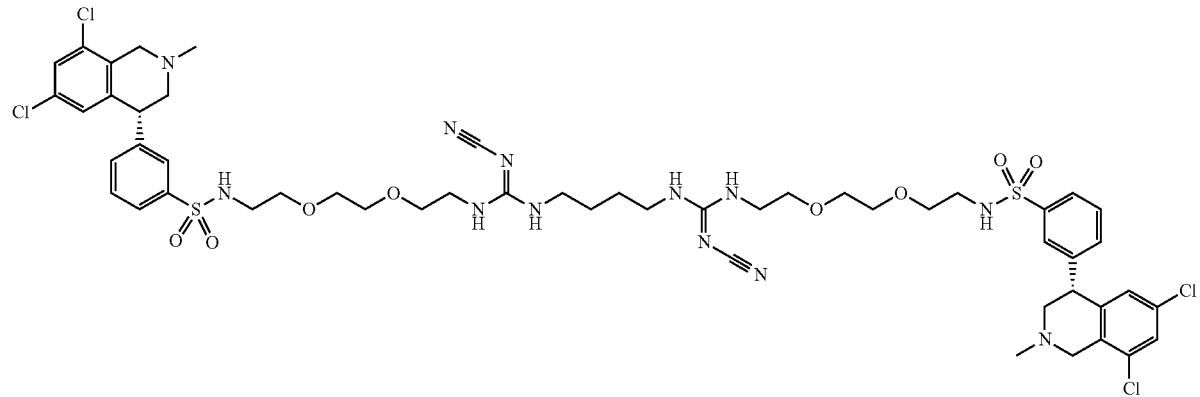

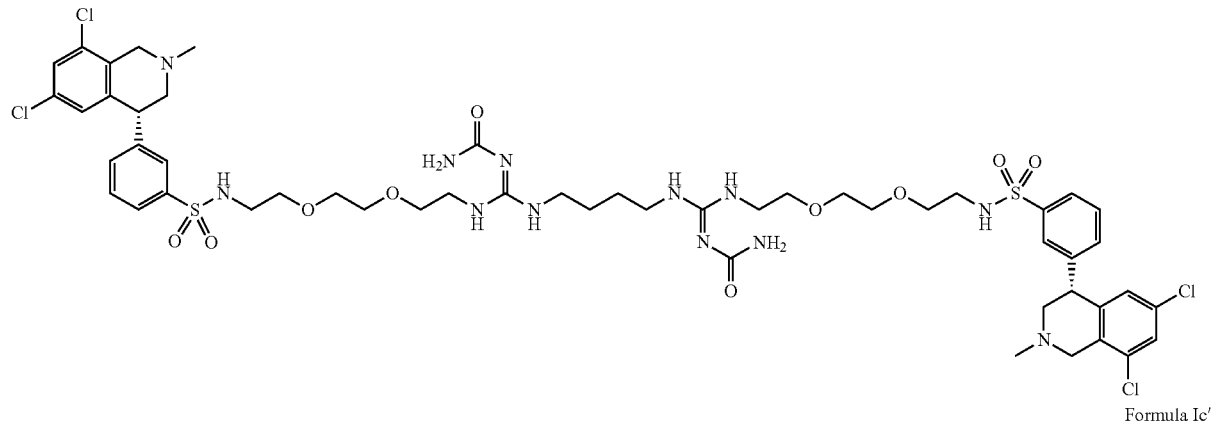

Formula Ib″

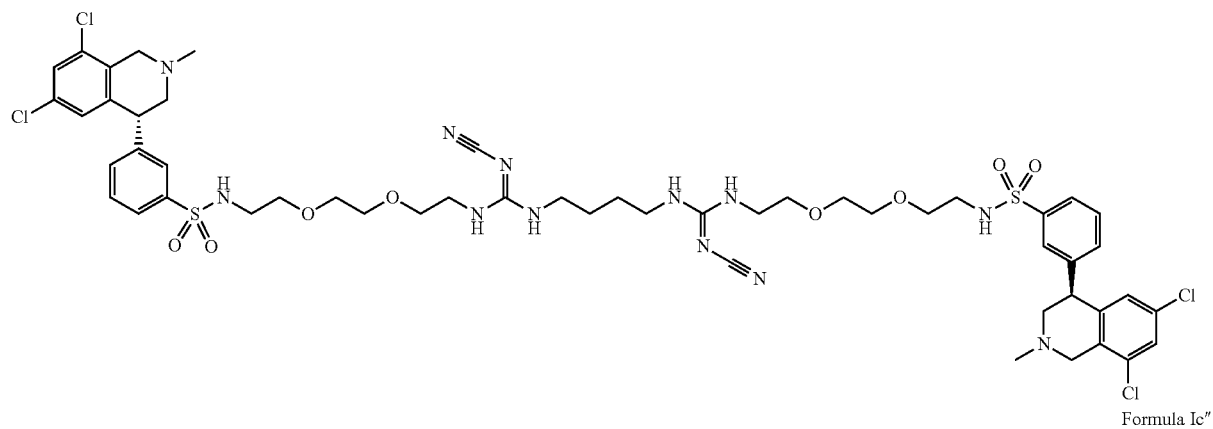

Formula Ic′

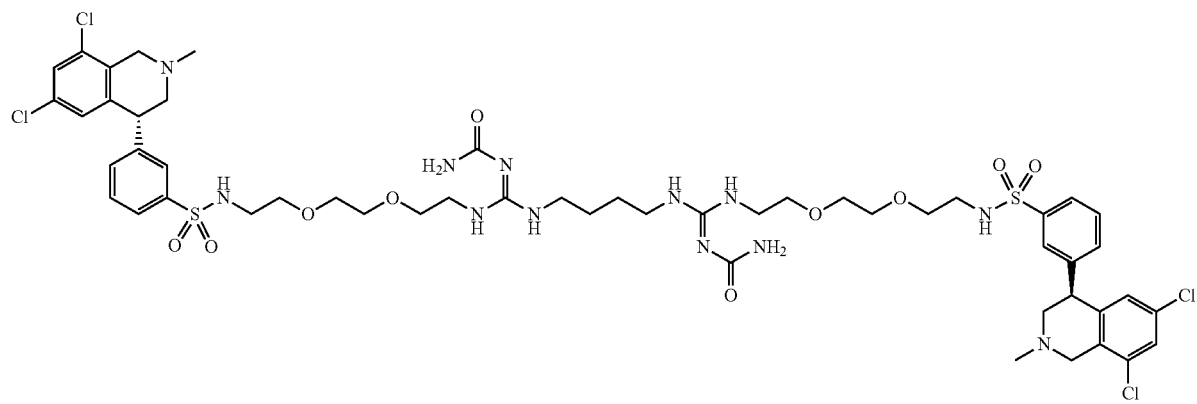

Formula Ic″ or pharmaceutically acceptable salts thereof.

Although the present invention contemplates all individual enantiomers and diasteromers, as well as mixtures of the enantiomers of said compounds, including racemates, the compound of Formula Ia′ and Formula Ia″, and pharmaceutically acceptable salts thereof, are particularly preferred. In particular, the dihydrochloride salt of the compound of Formula Ia″ is preferred.

Individual enantiomers may be separated or resolved by one of ordinary skill in the art at any convenient point in the synthesis of compounds of the invention, by methods such as selective crystallization techniques, chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994), or supercritical fluid chromatography (SFC) (See for example, T. A. Berger; "*Supercritical Fluid Chromatography Primer*," Agilent Technologies, July 2015).

A pharmaceutically acceptable salt of a compound of Formula I can be formed, for example, by reaction of an appropriate free base form of a compound of Formula I and an appropriate pharmaceutically acceptable acid in a suitable solvent under standard conditions well known in the art (See, for example, Bastin, R. J., et al.; *Org. Process. Res. Dev.*, 4, 427-435, 2000 and Berge, S. M., et al.; *J. Pharm. Sci.*, 66, 1-19, 1977). In particular, the preferred salt of a compound of Formula I is the dihydrochloride salt.

A pharmaceutically acceptable salt of a compound of Formula II can be formed, for example, by reaction of an appropriate free acid form of a compound of Formula II and an appropriate pharmaceutically acceptable base in a suitable solvent under standard conditions well known in the art (See, for example, Bastin, R. J., et al.; *Org. Process. Res. Dev.,* 4, 427-435, 2000 and Berge, S. M., et al.; *J. Pharm. Sci.,* 66, 1-19, 1977). In particular, a preferred salt of a compound of Formula II is the disodium salt.

WO2018/034883 describes a genus of compounds, including compounds of Formula II, which are inhibitors of the sodium-dependent phosphate cotransporter 2b (NPT2b or NaPiIIb). NPT2b is found on the luminal surface of the small intestine where it promotes phosphate absorption by active transport. A compound of Formula II can be prepared by methods described in WO2018/034883.

The compounds of Formula I, or salts thereof, may be prepared by a variety of procedures known to one of ordinary skill in the art, some of which are illustrated in the preparations, and examples below. The products of each step can be recovered by conventional methods well known in the art, including extraction, evaporation, precipitation, chromatography, filtration, trituration, and crystallization. The reagents and starting materials are readily available to one of ordinary skill in the art. Without limiting the scope of the invention, the following preparations, and examples are provided to further illustrate the invention. In addition, one of ordinary skill in the art appreciates that compounds of Formula I may be prepared by using starting materials or intermediates with the corresponding desired stereochemical configuration which can be prepared by one of skill in the art.

Certain abbreviations are defined as follows: "ACN" refers to acetonitrile; "BCECF-AM" refers to 2',7'-Bis(2-carboxyethyl)-5(6)-carboxyfluorescein acetoxymethyl ester; "BSA" refers to bovine serum albumin; "DCM" refers to methylene chloride or dichloromethane; "DMSO" refers to dimethyl sulfoxide; "EtOAc" refers to ethyl acetate; "ES/MS" refers to Electrospray Mass Spectrometry; "EMS" refers to ethyl methanesulfonate; "EtOH" refers to ethanol or ethyl alcohol; "FBS" refers to fetal bovine serum; "h" refers to hour or hours; "HEPES" refers to 4-(2-hydroxyethyl)-1-piperazineethane sulfonic acid; "HPLC" refers to high-performance liquid chromatography; "IC50" refers to the inhibitor concentration at half-maximal inhibition; "LC-MS" refers to liquid chromatography—mass spectrometry; "MeOH" refers to methanol; "min" refers to minute or minutes; "MTBE" refers to methyl tert-butyl ether; "m/z" refers to mass-to-charge ratio; "Pd(dba)$_2$" refers to bis (dibenzylideneacetone)palladium(0); "RT" refers to room temperature; "TLC" refers to thin layer chromatography.

LC-MS is performed on an AGILENT® HP1260 liquid chromatography system. Mass spectrometry measurements are accomplished by ES/MS (acquired in positive and/or negative mode) and are performed on a Mass Selective Detector quadrupole mass spectrometer interfaced to an HPLC which may or may not have an ELSD. LC-MS conditions (low pH): column: PHENOMENEX® GEMINI® NX C18 2.0×50 mm 3.0 μm, 110 Å; gradient: 5-95% B in 1.5 min, then 95% B for 0.5 min column temperature: 50° C.+/−10° C.; flow rate: 1.2 mL/min; 1 μL injection volume; Solvent A: deionized water with 0.1% HCOOH; Solvent B: ACN with 0.1% formic acid; wavelength 200-400 nm and 212-216 nm. If the HPLC is equipped with an ELSD the settings are 45° C. evaporator temperature, 40° C. nebulizer temperature, and 1.6 SLM gas flow rate. Alternate LC-MS conditions (high pH): column: Waters xBridge® C18 column 2.1×50 mm, 3.5 μm; gradient: 5-95% B in 1.5 min, then 95% B for 0.50 min; column temperature: 50° C.+/−10° C.; flow rate: 1.2 mL/min; 1 μL injection volume; Solvent A: 10 mM NH$_4$HCO$_3$, pH 9; Solvent B: ACN; wavelength: 200-400 nm and 212-216 nm; if had ELSD: 45° C. evaporator temp, 40° C. nebulizer temp, and 1.60 SLM gas flow rate.

Preparation 1

4-(3-Benzylsulfanylphenyl)-6,8-dichloro-2-methyl-3,4-dihydro-1H-isoquinoline

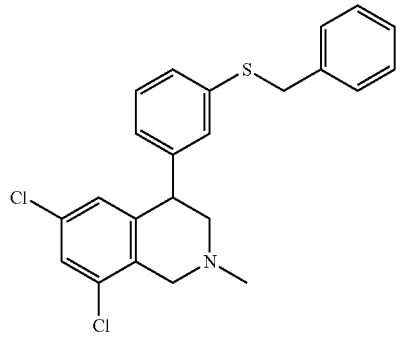 [SMILES: CN1Cc2c(Cl)cc(Cl)cc2C(c2cccc(SCc3ccccc3)c2)C1]

Set up three reactions in parallel on the same scale. For each reaction, prepare two solutions, Solution 1 and Solution 2. Solution 1: To a solution of 4-(3-bromophenyl)-6,8-dichloro-2-methyl-3,4-dihydro-1H-isoquinoline (54.0 g, 145.5 mmol) in xylene (1.08 L), add Pd(dba)$_2$ (3.35 g, 5.82 mmol) and Xantphos (3.37 g, 0.04 equiv 5.82 mmol) at 15° C. under nitrogen. Stir the mixture for 1 h. Solution 2: To a mixture of K$_2$CO$_3$ (10.1 g, 72.7 mmol) in xylene (1.08 L) add phenylmethanethiol (27.1 g, 218.3 mmol) dropwise at 0° C. under nitrogen. Stir the mixture for 1 h at 15° C. Add Solution 1 dropwise to Solution 2 at 15° C. and stir the mixture at 140° C. for 12 h.

Combine the three reaction mixtures and wash with water (500 mL). Concentrate the organic layer and purify by silica gel chromatography using a gradient of 1 to 17% EtOAc in petroleum ether to give the title compound (92 g, 50%).
$^1$H-NMR (400 MHz, CDCl$_3$) δ 7.28-7.17 (m, 8H), 7.05-7.04 (m, 1H), 7.00-6.95 (m, 1H), 6.74-6.69 (m, 1H), 4.15-4.04 (m, 3H), 3.76 (d, J=16.0 Hz, 1H), 3.47 (d, J=16.0 Hz, 1H), 2.90 (dd, J=11.2, 7.2 MHz, 1H), 2.50-2.42 (m, 4H).

Preparation 2

3-(6,8-Dichloro-2-methyl-3,4-dihydro-1H-isoquinolin-4-yl)benzenesulfonyl chloride; Hydrochloride Salt

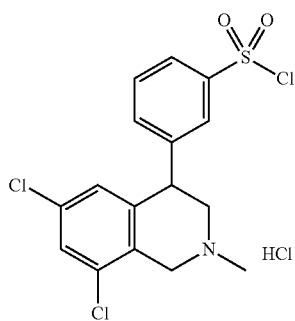 [SMILES: CN1Cc2c(Cl)cc(Cl)cc2C(c2cccc(S(=O)(=O)Cl)c2)C1 ; Cl]

Set up two reactions in parallel on the same scale. For each reaction, to a stirred mixture of 4-(3-benzylsulfanylphenyl)-6,8-dichloro-2-methyl-3,4-dihydro-1H-isoquinoline (50.0 g, 121 mmol), acetic acid (52.17 g, 868.8 mmol), and water (62 mL) in ACN (690 mL) add 1,3-dichloro-5,5-dimethyl-imidazolidine-2,4-dione (47.5 g, 241 mmol) portionwise at 0° C. Stir the mixture at 0 to 5° C. for 2 h, then concentrate the reaction mixture in-vacuo. Add MTBE (200 mL) and HCl (4 M solution in 1,4-dioxane, 10 mL) to each reaction and combine the reaction mixtures together. Stir for 30 min and collect the solid by filtration. Wash the solid with MTBE (100 mL) to give the title compound (112 g) which is used without further purification. Assuming quantitative yield, purity is estimated at 92% w/w based on a theoretical yield of 103 g. TLC (1:6 EtOAc:petroleum ether) $R_f$=0.05.

Preparation 3 tert-Butyl N-[2-[2-[2-[[3-[(4S)-6,8-dichloro-2-methyl-3,4-dihydro-1H-isoquinolin-4-yl]phenyl]sulfonylamino]ethoxy]ethoxy]ethyl]carbamate

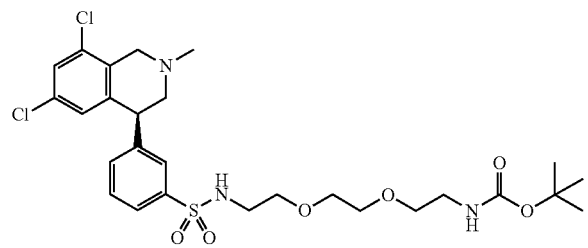 [SMILES: CN1Cc2c(Cl)cc(Cl)cc2[C@H](c2cccc(S(=O)(=O)NCCOCCOCCNC(=O)OC(C)(C)C)c2)C1]

To a solution of tert-butyl N-[2-[2-(2-aminoethoxy)ethoxy]ethyl]carbamate (5.22 g, 21.0 mmol) and trimethylamine (6.38 g, 8.79 mL, 63.0 mmol, 3.00 equiv.) in anhydrous DCM (120 mL) add racemic 3-(6,8-dichloro-2-methyl-3,4-dihydro-1H-isoquinolin-4-yl)benzenesulfonyl chloride (Abacipharm, 8.21 g, 21.0 mmol) and stir at RT under nitrogen overnight. Concentrate the reaction mixture in-vacuo. To the oily residue add EtOAc (50 mL), filter off solids and concentrate the filtrate in-vacuo to obtain an orange oil. Purify by silica gel column chromatography eluting with EtOAc to obtain the racemic compound (6.92 g, 55%) as a colorless oil. $^1$H-NMR (400 MHz, CDCl$_3$) δ 7.75 (d, J=8.0 Hz, 1H), 7.67 (s, 1H), 7.44 (t, J=7.6 Hz, 1H), 7.36 (d, J=7.2 Hz, 1H), 7.23 (d, J=2.0 Hz, 1H), 6.71 (d, J=1.2 Hz, 1H), 5.42-5.05 (br m, 1H), 4.29 (t, J=6.0 Hz, 1H), 3.73 (d, J=16.2 Hz, 1H), 3.57 (d, J=15.8 Hz, 1H), 3.55-3.46 (m, 8H), 3.34-3.25 (m, 2H), 3.14-3.08 (m, 2H), 2.97 (dd, J=11.5, 5.29 Hz, 1H), 2.59 (dd, J=11.5, 7.2 Hz, 1H), 2.46 (s, 3H), 1.41 (s, 9H).

Separate enantiomers on a Chiralpak® AD (8×35 cm) column (flow rate 400 mL/min, detection at 260 nm) in 11 injections of 629 mg eluting with 95:5 EtOH:ACN to obtain the title compound (2.94 g, 23%) as the second-eluting isomer. Chiral HPLC (column: Chiralpak® AD-H 4.6×150 mm, flow rate: 0.6 mL/min, detection: 250 nm, eluent: 95:5 EtOH:ACN) indicates >99% ee.

Alternative Synthesis

To a solution of tert-butyl N-[2-[2-(2-aminoethoxy)ethoxy]ethyl]carbamate (57.1 g, 230 mmol) in DCM (1.70 L) add triethylamine (65.2 g, 645 mmol) at 0° C. Add 3-(6,8-dichloro-2-methyl-3,4-dihydro-1H-isoquinolin-4-yl)benzenesulfonyl chloride; hydrochloride salt (material prepared according to Preparation 2; 84.0 g, 181 mmol) portionwise to the mixture at 0° C. Warm the mixture up to 25° C. and stir for 4 h. Combine the reaction mixture with two reaction mixtures prepared essentially as above starting with 3-(6,8-dichloro-2-methyl-3,4-dihydro-1H-isoquinolin-4-yl)benzenesulfonyl chloride; hydrochloride salt (material prepared according to Preparation 2; 52 g, 112 mmol each for a total of 104 g, 224 mmol). Pour the resulting mixture into ice water (1.8 L), then wash the organic layer with water (2×1.5 L) and concentrate to give a yellow residue. Purify by silica gel chromatography using a gradient of 1 to 2% MeOH in DCM to give the racemic compound (157 g, 64% yield) as a yellow oil.

Combine this racemic material (157 g, 261 mmol) with additional racemic material (23 g, 38 mmol) prepared as above. Separate enantiomers by SFC using a Chiralpak® AD-H (5 μm, 3×25 cm) column (flow rate 70 g/min, UV detection at 220 nM) eluting with 70:30 CO$_2$:(0.1% NH$_4$OH) in MeOH to obtain the title compound (50 g, 28%) as a yellow gum, second-eluting isomer, >99% ee. ES/MS m/z ($^{35}$Cl/$^{37}$Cl) 602/604 [M+H]$^+$.

Preparation 4

N-[2-[2-(2-aminoethoxy)ethyl]-3-[(4S)-6,8-dichloro-2-methyl-3,4-dihydro-1H-isoquinolin-4-yl]benzenesulfonamide dihydrochloride

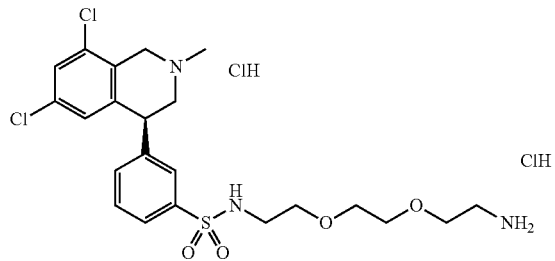 [SMILES: CN1Cc2c(Cl)cc(Cl)cc2[C@H](c2cccc(S(=O)(=O)NCCOCCOCCN)c2)C1 ; Cl ; Cl]

To tert-butyl N-[2-[2-[2-[[3-[(4S)-6,8-dichloro-2-methyl-3,4-dihydro-1H-isoquinolin-4-yl]phenyl]sulfonylamino]ethoxy]ethoxy]ethyl]carbamate (2.94 g, 4.88 mmol) add 4M hydrogen chloride in 1,4-dioxane (10 mL, 40 mmol) and stir the resulting solution at RT overnight. Concentrate the reaction mixture in vacuo to obtain a white foam (2.85 g, >100%). Dry under high vacuum overnight and use without further manipulation. ES/MS m/z ($^{35}$Cl/$^{37}$Cl) 502/504 [M+H]$^+$ Preparation 5

N-[2-[2-(2-aminoethoxy)ethoxy]ethyl]-3-[(4S)-6,8-dichloro-2-methyl-3,4-dihydro-1H-isoquinolin-4-yl] benzenesulfonamide

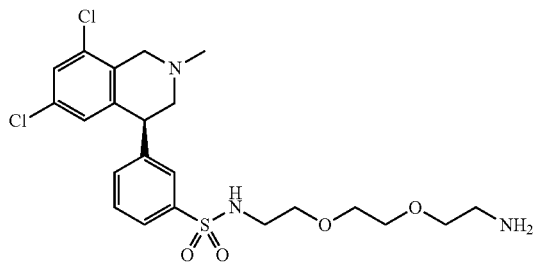 [SMILES: CN1Cc2c(Cl)cc(Cl)cc2[C@H](c2cccc(S(=O)(=O)NCCOCCOCCN)c2)C1]

Purify N-[2-[2-(2-aminoethoxy)ethoxy]ethyl]-3-[(4S)-6,8-dichloro-2-methyl-3,4-dihydro-1H-isoquinolin-4-yl]benzenesulfonamide dihydrochloride (992 mg, 1.84 mmol) using a 10 g Isolute® SCX column to obtain 740 mg of the free base as a clear colorless semi-solid (740 mg, 80%).

Preparation 6

N-[2-[2-(2-aminoethoxy)ethoxy]ethyl]-3-[(4S)-6,8-dichloro-2-methyl-3,4-dihydro-1H-isoquinolin-4-yl] benzenesulfonamide

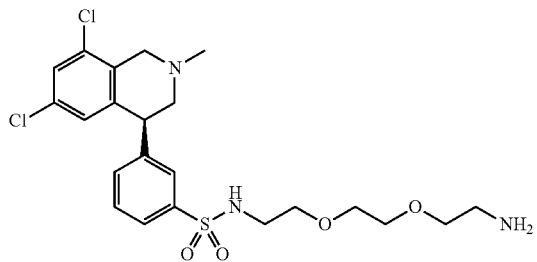 [SMILES: CN1Cc2c(Cl)cc(Cl)cc2[C@H](c2cccc(S(=O)(=O)NCCOCCOCCN)c2)C1]

To tert-butyl N-[2-[2-[2-[[3-[(4S)-6,8-dichloro-2-methyl-3,4-dihydro-1H-isoquinolin-4-yl]phenyl]sulfonylamino] ethoxy]ethoxy]ethyl]carbamate (48 g, 80 mmol) in MeOH (190 mL) at 15° C., add 4 M hydrochloric acid in 1,4-dioxane (100 mL, 400 mmol) and stir the resulting solution at RT overnight. Remove the solvents in-vacuo and dissolve the residue in water (150 mL). Add 5N NaOH (30 mL) and 2N NaOH (50 mL) to this solution until pH 9-10, then add 20% aqueous Na$_2$CO$_3$ (75 mL) to bring the solution to pH 11. Extract the aqueous mixture with EtOAc (2×200 mL, then 1×100 mL). Combine the organics and wash with a mixture of saturated aqueous sodium chloride (120 mL) and 20% Na$_2$CO$_3$ (30 mL). Dry the organics over sodium sulfate, filter, and concentrate in-vacuo. Dissolve the residue in toluene and concentrate in-vacuo, then repeat this operation two more times. Dissolve the residue in DCM and concentrate in-vacuo, then repeat this operation two more times to obtain a dark yellow oil (42 g, 94%), purity approximated at 90 wt % based on $^1$H-NMR comparison with anisole as an internal standard. $^1$H-NMR (400 MHz, CDCl$_3$) δ 7.76-7.72 (m, 1H), 7.68-7.66 (m, 1H), 7.43 (t, J=7.6 Hz, 1H), 7.36-7.33 (m, 1H), 7.23 (d, J=2.1 Hz, 1H), 6.74-6.72 (m, 1H), 4.28-4.22 (m, 1H), 3.67 (d, J=16.2 Hz, 1H), 3.62-3.49 (m, 9H), 3.11 (t, J=4.6 Hz, 2H), 2.91 (dd, J=11.8, 5.5 Hz, 1H), 2.87 (t, J=5.1 Hz, 2H), 2.58 (dd, J=11.7, 7.4 Hz, 1H), 2.44 (s, 3H). ES/MS m/z ($^{35}$Cl/$^{37}$Cl) 502/504 [M+H]$^+$.

EXAMPLE 1

2-Cyano-1-[4-[[N'-cyano-N-[2-[2-[2-[[3-[(4S)-6,8-dichloro-2-methyl-3,4-dihydro-1H-isoquinolin-4-yl] phenyl]sulfonylamino]ethoxy]ethoxy]ethyl]carbamimidoyl]amino]butyl]-3-[2-[2-[2-[[3-[(4S)-6,8-dichloro-2-methyl-3,4-dihydro-1H-isoquinolin-4-yl] phenyl]sulfonylamino]ethoxy]ethoxy]ethyl] guanidine

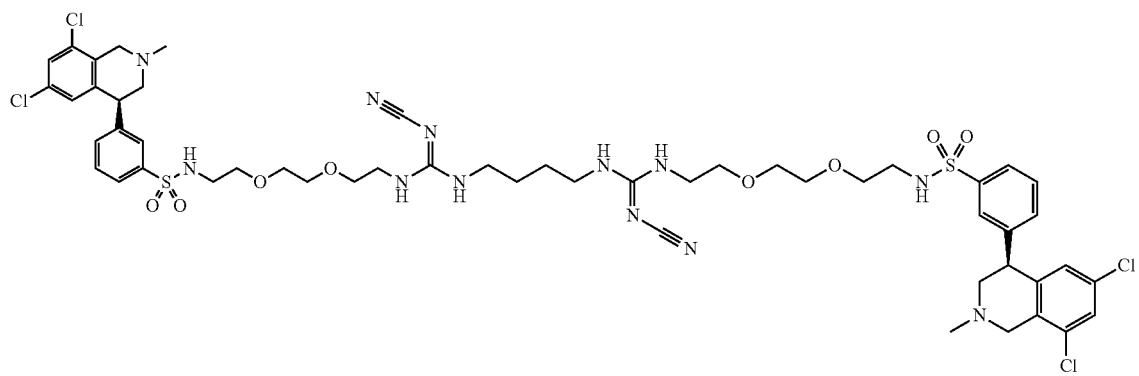 [SMILES: CN1Cc2c(Cl)cc(Cl)cc2[C@H](c2cccc(S(=O)(=O)NCCOCCOCCN/C(=N\C#N)NCCCCN/C(=N/C#N)NCCOCCOCCNS(=O)(=O)c3cccc([C@@H]4CN(C)Cc5c(Cl)cc(Cl)cc54)c3)c2)C1]

To a solution of N-[2-[2-(2-aminoethoxy)ethoxy]ethyl]-3-[(4S)-6,8-dichloro-2-methyl-3,4-dihydro-1H-isoquinolin-4-yl]benzenesulfonamide (prepared according to Preparation 5; 740 mg, 1.47 mmol) in 1,4-dioxane (10 mL) and pyridine (10 mL) add diphenoxymethylenecyanamide (351 mg, 1.47 mmol) and stir at RT under nitrogen overnight. Add butane-1,4-diamine (65 mg, 0.74 mmol) and heat at 60° C. for 24 h, then heat at 90° C. overnight. Cool the reaction mixture to RT. Dilute the reaction mixture with EtOAc, wash with 5% aqueous potassium carbonate twice, dry over anhydrous magnesium sulfate, filter and concentrate in-vacuo to obtain an orange oil. Purify the crude mixture by silica gel column chromatography eluting with a gradient of 0 to 10% MeOH in DCM to obtain the title compound as a yellow foam (591 mg, 67%). ES/MS m/z ($^{35}$Cl) 1193 [M+H]$^+$ Alternative Synthesis To a solution of N-[2-[2-(2-aminoethoxy)ethoxy]ethyl]-3-[(4S)-6,8-dichloro-2-methyl-3,4-dihydro-1H-isoquinolin-4-yl]benzenesulfonamide (prepared according to Preparation 6; 90 wt % purity, 24.5 g, 44 mmol) in 1,4-dioxane (240 mL) add pyridine (17.7 mL, 219 mmol) and diphenoxymethylenecyanamide (10.5 g, 44 mmol) and stir at RT under nitrogen overnight. To the reaction mixture, add butane-1,4-diamine (1.93 g, 21.9 mmol), split the reaction into four equal portions, and heat each portion to 90° C. for 21 h. Add butane-1,4-diamine (102 mg, 1.16 mmol) and 1,4-dioxane (5 mL) to each portion of the reaction and continue heating at 90° C. for 23 h. Add butane-1,4-diamine (42 mg, 0.48 mmol) and 1,4-dioxane (5 mL) to portions of the reaction mixture showing greater than a 1:5 ratio of cyanoisourea intermediate:title compound as determined by LC-MS. Continue heating all portions of the reaction mixture at 90° C. overnight and then cool to RT. Combine the reaction portions. Combine the mixture with two other batches prepared in essentially the same way using N-[2-[2-(2-aminoethoxy)ethoxy]ethyl]-3-[(4S)-6,8-dichloro-2-methyl-3,4-dihydro-1H-isoquinolin-4-yl]benzenesulfonamide (90 wt % purity) (10.05 g, 18.00 mmol and 5.20 g, 9.32 mmol respectively). Remove the solvents under reduced pressure, dissolve the residue in DCM (250 mL), then wash the organics with 5% aqueous potassium carbonate (2×80 mL). Combine the aqueous washes and extract with DCM (2×40 mL). Combine all organic washes together and wash with saturated aqueous sodium chloride (80 mL). Dry the organics over anhydrous sodium sulfate, filter, and concentrate under reduced pressure to obtain a yellowish brown oil. Purify the crude material by silica gel column chromatography eluting with a gradient of 8 to 16% EtOH in DCM. Then re-purify the material twice by silica gel chromatography eluting with gradients of 5 to 12% and 2 to 12% MeOH in DCM. Re-purify impure fractions by silica gel chromatography with a gradient of 2 to 12% MeOH in DCM and combine pure materials to obtain the title compound as an off-white foamy solid (15.3 g, 36%). ES/MS m/z ($^{35}$Cl) 1193 [M+H]$^+$.

EXAMPLE 2

[[4-[[N'-Carbamoyl-N-[2-[2-[2-[[3-[(4S)-6,8-dichloro-2-methyl-3,4-dihydro-1H-isoquinolin-4-yl]phenyl]sulfonylamino]ethoxy]ethoxy]ethyl]carbamimidoyl]amino]butylamino]-2-[2-[2-[[3-[(4S)-6,8-dichloro-2-methyl-3,4-dihydro-1H-isoquinolin-4-yl]phenyl]sulfonylamino]ethoxy]ethoxy]ethylamino]methylene]urea dihydrochloride

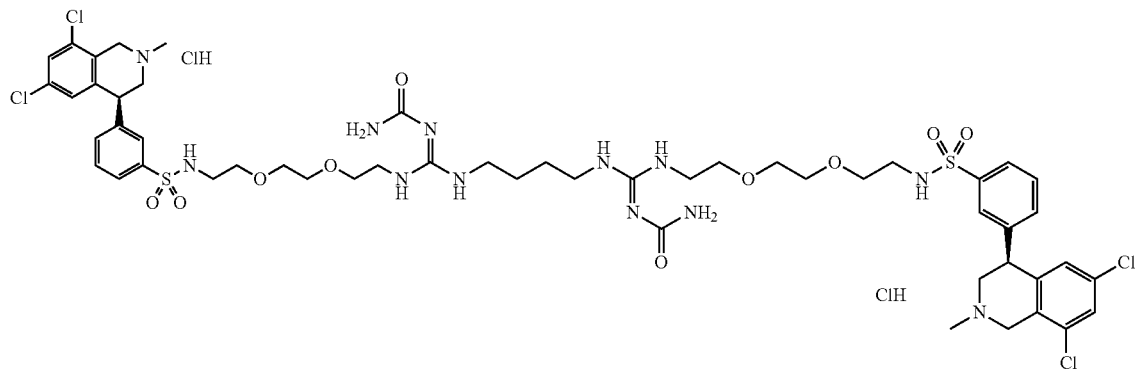 [SMILES: CN1Cc2c(Cl)cc(Cl)cc2[C@H](c2cccc(S(=O)(=O)NCCOCCOCCN/C(=N\C(N)=O)NCCCCN/C(=N/C(N)=O)NCCOCCOCCNS(=O)(=O)c3cccc([C@@H]4CN(C)Cc5c(Cl)cc(Cl)cc54)c3)c2)C1 ; Cl ; Cl]

To Example 1 (670 mg, 0.562 mmol) add trifluoroacetic acid (10 mL) and water (1 mL) and stir at RT overnight. Remove volatiles under reduced pressure. Dissolve residue in a minimum amount of MeOH and purify through a 10 g Isolute® SCX column to obtain a yellow foam (629 mg). Purify by preparative HPLC [column: Phenomenex® Kinetex® EVO C$_{18}$ 100×30 mm, 5 μm particle size, inline heater at 50° C.; eluent: 51 to 86% (5% MeOH in 10 mM NH$_4$HCO$_3$) in ACN] to obtain the title compound as a free base as an orange oil (253 mg, 37%). ES/MS m/z ($^{35}$Cl) 1229 [M+H]$^+$. In a vial, dissolve the free base compound (223 mg, 0.181 mmol) in DCM (0.5 mL) and add hydrochloric acid (1M solution in diethyl ether, 1 mL) drop wise with shaking. White solids precipitate out of solution. Shake the mixture for 5 min and then concentrate in-vacuo to obtain the title compound as a fine white powder (236 mg, 100%). ES/MS m/z ($^{35}$Cl) 1229 [free base M+H]$^+$, 1227 [free base M−H]$^+$ Alternative Synthesis Prepare two mixtures of equal portions in the following manner: For each portion, mix the compound of Example 1 (5.1 g, 4.3 mmol), 4 M hydrochloric acid in dioxane (50 mL, 200 mmol) and water (25 mL). Heat each solution to 65° C. for 2 h. Cool the mixtures to RT and stir at RT overnight, then combine them together with another batch prepared in essentially the same manner starting with the compound of Example 1 (3.1 g, 2.6 mmol). Concentrate the mixture in-vacuo. Add water/EtOH (1:2, 100 mL) to the residue and concentrate in-vacuo. Repeat this operation three times. To the residue add EtOH and stir at 45° C. for 10 min, then concentrate in-vacuo. Repeat this operation three times. Dry the residue in-vacuo at RT for 22 h. To the residue, add another batch of product prepared in essentially the same manner as described above with Example 1 (1 g, 0.8 mmol). Dry in-vacuo at RT for 23 h, 50° C. 16 h, 55° C. 6 h, and at RT for 72 h to yield the title compound (14.7 g, 94%). ES/MS m/z ($^{35}$Cl) 1229 [free base M+H]$^+$.

Assays

In Vitro NHE3 Inhibition Activity

To create an NHE3 assay, cells selectively expressing NHE3 are generated by overexpressing human NHE3 in an endogenously NHE-deficient cell line. The NHE-deficient cell line is created by chemical-induced mutagenesis. After the mutagenesis, NHE-deficient cells are selected by subjecting lithium (Li) loaded cells to an acidic extracellular environment. Under these conditions, NHE exchanges intracellular Li$^+$ for extracellular protons, thus only NHE-deficient cells can avoid a toxic intracellular acidosis and survive.

An NHE-deficient cell line, NHD C8, is generated by mutagenesis and selection from the cell line Dede (ATCC® CCL-39™). The mutagenesis is induced by treating Dede CCL-39 cells with EMS (Sigma-Aldrich) in growth media at a final concentration of 500 µg/ml for 20 h. NHE-deficient cells are selected by culturing in a LiCl solution (130 mM LiCl, 5 mM KCl, 1 mM MgSO$_4$, 2 mM CaCl$_2$, 5 mM glucose and 20 mM Hepes-Tris, pH 7.4) for 2 h followed by culturing in a choline chloride solution (130 mM choline chloride, 5 mM KCl, 1 mM MgSO$_4$, 2 mM CaCl$_2$, and 20 mM 2-(N-morpholino) ethanesulfonic acid-Tris, pH 5.5) for 30 min. The surviving cells after growing in standard culture media to 90% confluence are subjected to a second cycle of selection. Single-clone colonies are isolated, grown to full confluence, and are subjected to a third cycle of selection. Surviving clones are expanded and tested for the activity of sodium-hydrogen exchanger (see assay below).

The cDNA encoding human NHE3 with a myc-tag is subcloned into plasmid pcDNA3.1, and a stable cell line is generated in the above-mentioned NHE-deficient NHD C8 cells. Stably NHE3 over-expressing cells are maintained in McCoy's 5A medium (Hyclone-GE Healthcare Bio science) with 10% FBS, 400 mg/ml G418 (Gibco-ThermoFisher Scientific), and antibiotic/antimycotic solution.

To measure NHE activity, the intracellular pH of the cells is reduced by addition of NH$_4$Cl. The sodium-dependent intracellular pH change is then measured by the intracellular pH-sensitive fluorescein dye, BCECF-AM (Molecular Probes-ThermoFisher Scientific). NHD8/NHE3 cells are dispersed with a multi-channel pipette into 96-well poly-D-lysine plates (Corning) at 30,000 per well. The cells are incubated at 37° C. plus 5% CO$_2$ for 24 h. Cell culture media are aspirated, cells are washed with 100 µl of NaCl-HEPES solution (100 mM NaCl, 10 mM glucose, 5 mM KCl, 2 mM CaCl$_2$, 1 mM MgCl$_2$, 0.1% BSA, 50 mM HEPES, pH 7) twice, and then cells are incubated with 100 µl of 5 µM BCECF-AM in NH$_4$Cl/pluronic F-127/probenecid solution (130 mM NH$_4$Cl, 5 mM KCl, 2 mM CaCl$_2$, 1 mM MgCl$_2$, 0.1% BSA, 0.0625% pluronic F-127, 2 mM probenecid, 20 mM HEPES, pH 7) for 60 min at RT. Following the incubation, cells are washed with 100 µl of ammonium free, sodium free, HEPES/0.1% BSA solution (100 mM choline chloride, 10 mM glucose, 5 mM KCl, 2 mM CaCl$_2$, 1 mM MgCl$_2$, 0.1% BSA, 50 mM HEPES, pH 7) twice. 86 µl of ammonium free, sodium free, HEPES/0.1% BSA containing 30 µM amiloride with compound or controls are then added to the appropriate wells. The NHE activity is initiated by the addition of 14 µl of 1M NaCl to achieve a final concentration of 140 mM. The plate is immediately read for fluorescent intensity at an excitation wavelength of 505 nm and emission wavelength of 550 nm. Percentage of inhibition at each concentration tested is calculated relative to NHE activity with 1% DMSO as 0% inhibition and NHE activity with a saturating concentration of a standard inhibitor as 100% inhibition. A 9-concentration response curve from 1000 nM to 0.152 nM plus no compound is fitted to a 4-parameter model using Prism to determine the IC$_{50}$.

Example 2 inhibits human NHE3 in a concentration-dependent manner with an IC$_{50}$ of 5.76 nM (geometric mean of individual IC$_{50}$, n=7 with a standard error of geometric mean of 0.72). Example 2 is selective for NHE3, in that it was not a potent NPT2b (IC$_{50}$=58.4 µM) or SGLT1 (IC$_{50}$=6.6 µM) inhibitor. Example 1 inhibits human NHE3 in a concentration-dependent manner with an IC$_{50}$ of 37.9 nM (geometric mean of individual IC$_{50}$, n=2 with a standard error of geometric mean of 6.2).

Effect of Example 2 on Blood Pressure

Male spontaneously hypertensive (SHR) rats weighing 250-300 g with age of 7 weeks are acclimated to a reversed light cycle (8:00 am lights off and 8:00 pm lights on) and fed regular chow and water ad libitum. Implantable telemetry devices (model TA11PA-C40, Data Sciences International) are implanted into the abdominal aorta. After recovering from surgery, rats are placed in individual cages in a quiet telemetry facility room for measuring blood pressure (mean arterial pressure, MAP) and heart rate (HR). Digitized pressure signals are acquired for 20 second every 5 min using DSI Dataquest IV 4.0 software.

The 31 SHR rats are randomized by MAP into two groups and treated twice daily for 14 days with vehicle (n=15) (10% acacia, 0.05% antifoam in purified water) or 0.15 mg/kg/day Example 2. The first dose is given between 6:00 and 6:30 am (2 h prior to lights off) and the second dose is given between 4:00 and 4:30 pm. The daily food consumption and body weight gain are also monitored.

MAP, HR, and body weight (BW) data are analyzed by repeated measures analysis of covariance (ANCOVA) with baseline as the covariate. Food consumption (FC) data are analyzed by repeated measures analysis of variance (ANOVA). The mean blood pressure across the time course of the study (days 1-14) for the group treated with 0.15 mg/kg/day of Example 2 is 4.83 mm Hg less than that of the control group with a p-value of 0.0007 (Table 1). No significant effect is observed on HR, BW, or FC.

TABLE 1

Effect of Example 2 on mean arterial pressure (MAP) in male spontaneously hypertensive rats (SHR)

| Treatment group | Mean blood pressure over days 1-14 (mm Hg) | SEM | Difference (mm Hg) | p-value |
|---|---|---|---|---|
| Vehicle | 158.16 | 0.85 | 4.83 | 0.0007 |
| Example 2 0.15 mg/kg/day | 153.33 | 0.97 | | |

Effect of Example 1 on Sodium Absorption

Urinary sodium excretion following an oral bolus dose of sodium chloride is an indirect measure of sodium absorption in the intestine.

Male Sprague-Dawley with body weights ranging from 200 to 250 g are randomized into groups based on equal mean body weights. Henceforth the following formulation is referred to as "1% HEC": 1% hydroxyethyl cellulose (HEC) and 0.25% Tween® 80 with antifoam vehicle in water.

Example 1 at 0.1 mg/mL (final dose 1 mg/kg dosed in 10 mL/kg volume) is formulated with 1% HEC in a glass vial containing a pre-weighed amount of compound, and then probe sonicating until it appears as a uniform suspension. To ensure that the compound does not adhere to the sides or bottom of the vial, a stir bar is added to the bottle and the suspension is stirred throughout the formulation and dosing process. The subsequent dosing solutions of Example 1 are prepared by serial dilutions with 1% HEC. NaCl at 10 mg/ml (final dose 200 mg/kg dosed in 20 ml/kg volume) is formulated by adding sterile water.

On the day before the study, the animals are placed into clean cages without food but with access to water for an overnight fast. On the day of the study, rats are orally dosed with vehicle or varying doses of Example 1. 30 min later, animals are dosed with NaCl, then immediately transferred to metabolic cages. Urine samples are collected for 2 h. Net urine volume is recorded. Urinary sodium, and creatinine are assessed using a clinical biochemistry analyzer.

Values expressed as the ratio of urinary sodium to creatinine (mM/mM) are calculated and presented as mean±SEM. The curves are fitted with 4-parameter logistic curve fitting tool GraphPad Prism 6 to calculate the ED50. For the purpose of curve fitting, the dose of Example 1 is artificially set to 0.001 mg/kg in the software for the vehicle-alone group.

Following oral administration of Example 1 and a NaCl bolus, urinary sodium excretion decreases in a dose dependent fashion (Table 2). The $ED_{50}$ of Example 1 on urinary sodium excretion is 0.058 mg/kg. The dose-dependent decrease in urinary sodium excretion is consistent with a dose-dependent inhibition of intestinal sodium absorption with Example 1.

TABLE 2

Effect of Example 1 on Urinary Sodium in Rats

| Treatment | Urinary Sodium to Creatinine Ratio (mM/mM, Means ± SEM) |
| --- | --- |
| Vehicle (n = 8) | 1.43 ± 0.16 |
| Example 1, 0.03 mg/kg (n = 5) | 1.19 ± 0.19 |
| Example 1, 0.1 mg/kg (n = 5) | 0.80 ± 0.23 |
| Example 1, 0.3 mg/kg (n = 5) | 0.37 ± 0.06 |
| Example 1, 1.0 mg/kg (n = 5) | 0.63 ± 0.23 |

Effect of Example 2 on Sodium and Phosphate Absorption

Urinary sodium and phosphate excretion following an oral bolus dose of sodium phosphate is an indirect measure of sodium and phosphate absorption in the intestine.

Male Sprague-Dawley rats at an age of about 7 weeks with body weights ranging from 195 to 221 g are randomized into groups based on equal mean body weights. Example 2 at 0.3 mg/mL (final dose 3 mg/kg dosed in 10 mL/kg volume) is formulated by adding 1% HEC to a glass vial containing a pre-weighed amount of compound, and then probe sonicating until it appears as a uniform suspension. To ensure that the compound does not adhere to the sides or bottom of the vial, a stir bar is added to the bottle and the suspension is stirred throughout the formulation and dosing process. The subsequent dosing solutions of Example 2 are prepared by serial dilutions with 1% HEC. $NaH_2PO_4$ at 34.5 mg/ml (final dose 690 mg/kg dosed in 20 ml/kg volume) is formulated by adding sterile water.

On the day of the study, the animals are placed into clean cages without food but with access to water for a 4 h fast before the study. Rats are orally dosed with vehicle or varying doses of Example 2. 15 min later, animals are dosed with sterile water or $NaH_2PO_4$, then immediately transferred to metabolic cages. Urine samples are collected for 4 h. Net urine volume is recorded. Urinary sodium, creatinine, and phosphate are assessed using a clinical biochemistry analyzer. Values expressed as the ratio of urinary-to-dietary phosphorus or sodium are calculated and presented as mean±SEM. Curves are fitted with a 4-parameter logistic curve fitting tool GraphPod Prism 6 to calculate the ED50. For the purpose of curve fitting, the dose of Example 2 is artificially set to 0.00001 mg/kg in the software for the vehicle-alone group.

Following oral administration of Example 2 and a phosphate bolus, urinary sodium and phosphate excretion decrease in a dose dependent fashion (Table 3). The $ED_{50}$ of Example 2 on urinary phosphorus excretion is 0.041 mg/kg and $ED_{50}$ of Example 2 on sodium excretion is 0.058 mg/kg. The dose-dependent decrease in urinary sodium and phosphate excretion is consistent with a dose-dependent inhibition of intestinal sodium and phosphate absorption with Example 2.

TABLE 3

Effect of Example 2 on Urinary Phosphorus and Sodium in Rats

| Treatment | Ratio of Urinary-to-Dietary Phosphorus (Means ± SEM) | Ratio of Urinary-to-Dietary Sodium (Means ± SEM) |
| --- | --- | --- |
| Vehicle | 0.297 ± 0.039 | 0.271 ± 0.031 |
| Example 2, 0.001 mg/kg | 0.337 ± 0.017 | 0.326 ± 0.042 |
| Example 2, 0.003 mg/kg | 0.350 ± 0.023 | 0.413 ± 0.055 |
| Example 2, 0.01 mg/kg | 0.320 ± 0.042 | 0.290 ± 0.06 |
| Example 2, 0.03 mg/kg | 0.268 ± 0.04 | 0.276 ± 0.06 |
| Example 2, 0.1 mg/kg | 0.197 ± 0.045 | 0.105 ± 0.042 |
| Example 2, 0.3 mg/kg | 0.168 ± 0.027 | 0.039 ± 0.010 |
| Example 2, 1 mg/kg | 0.191 ± 0.039 | 0.051 ± 0.027 |
| Example 2, 3 mg/kg | 0.144 ± 0.009 | 0.022 ± 0.009 |

Effect of Example 2 in Combination with an NPT2b Inhibitor (Compound A) on Phosphate Absorption in Rats NPT2b inhibitor dosing solutions: Compound A and poly-1-vinylpyrrolidone-co-vinyl acetate (PVP-VA, Sigma-Aldrich) are weighed into a bottle at a ratio of 30% Compound A and 70% PVP-VA by weight. A clear yellow solution is prepared by diluting the mixture in MeOH followed by the addition of 2 mol NaOH per mol Compound A using 5 N NaOH. The solution is spray dried by a stream of hot nitrogen and the solid dispersion powder is collected and then further dried in a vacuum oven. Doses for the sprayed dried solid dispersion (SDD) are expressed as active pharmaceutical ingredient (API) throughout.

To make the Compound A dosing solution, an appropriate amount of Compound A SDD is weighed in a vial and dissolved in water (10 mL/kg dosing volume). To ensure that the compound does not adhere to the sides or bottom of the vial, a stir bar is added to the bottle and the suspension is stirred throughout the formulation and dosing processes. The subsequent solutions for lower doses are prepared by serial dilutions with water. PVP-VA at 7 mg/mL is used as a vehicle control.

NHE3 inhibitor dosing solutions: To make the Example 2 dosing solution, an appropriate amount of the compound is weighed in a vial and dissolved in 1% HEC (10 mL/kg dosing volume). To ensure that the compound does not adhere to the sides or bottom of the vial, a stir bar is added to the bottle and the suspension is stirred throughout the formulation and dosing processes. The subsequent solutions for lower doses are prepared by serial dilutions with HEC.

To make the radiolabeled phosphate dosing solution, a 16.25 mM $Na_2HPO_4$, 0.9% saline, pH 7.4 solution is prepared and filtered using a sterile, 0.22 μm, polyethersulfone, Millex-GP Syringe Filter Unit (EMD Millipore). Radioactive phosphate ($H_3^{33}PO_4$, Perkin Elmer) is added at about 2.5 μCi per mL of the solution and filtered again.

Three separate studies are performed. In these studies, male Sprague Dawley rats, are randomized into groups with approximately equal mean body weights. Following an overnight fast, all the animals are dosed at 10 mL/kg with either vehicle, varying doses of Compound A (Study 1), varying doses of Example 2 (Study 2) or 1.2 mg/kg Compound A and varying doses of Example 2 (Study 3). 15 min later, radiolabeled phosphate is orally dosed in a 2 mL volume. 15 min later, blood is collected and plasma is prepared. Radioactivity (dpm) in 50 μL plasma is measured by scintillation counting and is used to calculate phosphate absorption. The results are normalized with the vehicle controls representing 100% absorption. The curves are fitted with nonlinear regression with variable slope using GraphPad Prism 6 to calculate the $ED_{50}$ and $E_{max}$ given in Table 7. For the purposes of curve fitting in the $ED_{50}$ calculation, the dose of Example 2 is artificially set to 0.00001 mg/kg in the software for the vehicle-alone group in Study 2, and also for the vehicle+1.2 mg/kg Compound A group in Study 3. No curve fit was performed for Compound A alone in Study 1.

The results of the three separate studies performed in rats, a dose response study for Compound A (Study 1), a dose response study for Example 2 (Study 2) and a dose response study for Example 2 in the presence of 1.2 mg/kg Compound A (Study 3) are summarized in Tables 4-7 below. Example 2 and Compound A both inhibit phosphate absorption in a dose dependent fashion with a percent inhibition at the highest dose tested of 37% and 18%, respectively. However, when given in combination, an inhibition of 70% is achieved at the highest dose of Example 2 in combination with 1.2 mg/kg Compound A. Thus, the two compounds are more effective when dosed together than when either compound is dosed alone, consistent with each compound inhibiting distinct pathways contributing to intestinal phosphate absorption in rats.

TABLE 4

Effect of Compound A on Phosphate Absorption in Rats (Study 1)

| Treatment | Absorption (vs. vehicle control, %, means ± SEM) |
|---|---|
| Vehicle | 100 ± 7.23 |
| Compound A, 0.01 mg/kg | 94.39 ± 7.88 |
| Compound A, 0.1 mg/kg | 87.61 ± 6.08 |

TABLE 4-continued

Effect of Compound A on Phosphate Absorption in Rats (Study 1)

| Treatment | Absorption (vs. vehicle control, %, means ± SEM) |
|---|---|
| Compound A, 1 mg/kg | 87.64 ± 7.26 |
| Compound A, 10 mg/kg | 81.53 ± 5.50 |

TABLE 5

Effect of Example 2 on Phosphate Absorption in Rats (Study 2)

| Treatment | Absorption (vs. vehicle control, %, means ± SEM) |
|---|---|
| Vehicle | 100.00 ± 14.22 |
| Example 2, 0.001 mg/kg | 97.16 ± 20.76 |
| Example 2, 0.003 mg/kg | 100.81 ± 20.74 |
| Example 2, 0.01 mg/kg | 75.15 ± 15.52 |
| Example 2, 0.03 mg/kg | 83.17 ± 17.99 |
| Example 2, 0.1 mg/kg | 57.29 ± 11.20 |
| Example 2, 0.3 mg/kg | 71.09 ± 13.98 |
| Example 2, 1 mg/kg | 44.29 ± 9.09 |
| Example 2, 3 mg/kg | 60.04 ± 12.00 |
| Example 2, 10 mg/kg | 63.47 ± 8.39 |

TABLE 6

Effect of Compound A and Example 2 in Combination on Phosphate Absorption in Rats (Study 3)

| Treatment | Absorption (vs. vehicle control, %, means ± SEM) |
|---|---|
| Vehicle + Compound A, 1.2 mg/kg | 71.00 ± 11.63 |
| Example 2, 0.001 mg/kg ± Compound A, 1.2 mg/kg | 85.61 ± 5.16 |
| Example 2, 0.003 mg/kg ± Compound A, 1.2 mg/kg | 70.98 ± 7.27 |
| Example 2, 0.01 mg/kg ± Compound A, 1.2 mg/kg | 73.53 ± 7.29 |
| Example 2, 0.03 mg/kg + Compound A, 1.2 mg/kg | 61.82 ± 6.73 |
| Example 2, 0.1 mg/kg + Compound A, 1.2 mg/kg | 44.78 ± 6.09 |
| Example 2, 0.3 mg/kg + Compound A, 1.2 mg/kg | 35.56 ± 2.86 |
| Example 2, 1 mg/kg + Compound A, 1.2 mg/kg | 35.52 ± 8.67 |
| Example 2, 3 mg/kg + Compound A, 1.2 mg/kg | 26.94 ± 4.94 |
| Example 2, 10 mg/kg + Compound A, 1.2 mg/kg | 29.83 ± 3.72 |

TABLE 7

| | Compound A | Example 2 | Example 2 ± 1.2 mg/kg Compound A |
|---|---|---|---|
| $ED_{50}$ (mg/kg) | No curve fit | 0.041 | 0.056 |
| % Inhibition at the highest dose | 18% | 37% | 70% |

Effect of Example 2 in Combination with an NPT2b Inhibitor (Compound A) on Phosphate Absorption and Intestinal Phosphate Retention in Rats The purpose of this study is to investigate in rats the effect of Example 2, Compound A, and an Example 2/Compound A combination on phosphate absorption 15 min after dosing the compounds and the phosphate retained in the intestine 4.25 h after dosing the compounds. The latter is a measure of the oral phosphate load which is absorbed over an extended period.

Two vehicles are used in this study: 1) 1% HEC and 2) 0.46% poly-1-vinylpyrrolidone-co-vinyl acetate in water (PVP-VA vehicle). The vehicle control group in this study receives a 1:1 combination of the two vehicles.

The Example 2, Compound A and phosphate dosing solutions are prepared similarly as described above, except the doses are 0.4 mg/kg for Example 2 and 10 mg/kg for Compound A and they are prepared at a concentration where they would be dosed in a 5 mL/kg volume. The Example 2 and Compound A alone groups are mixed 1:1 with the vehicle of the other compound, while the Compound A and Example 2 are mixed 1:1 prior to dosing. The final dosing volume is 10 mL/kg in all cases.

Male Sprague Dawley rats are fasted 4 h and then administered appropriate vehicles, 10 mg/kg Compound A, 0.4 mg/kg Example 2, or a combination of both compounds. 15 min later, the animals are dosed with radiolabeled phosphate solution. 15 min later, blood is collected and plasma is prepared. Radioactivity in plasma is measured by scintillation counting and used to calculate the inhibition of phosphate absorption. While Example 2 (0.4 mg/kg) inhibits phosphate absorption by 29% (P=0.046 versus vehicle control) and Compound A (10 mg/kg) inhibits phosphate absorption by 35% (P=0.013 versus vehicle control), the combination of the two compounds inhibits phosphate absorption by 63% (P=0.0001 versus vehicle control). The 63% inhibition by the Example 2/Compound A combination exceeds the inhibition by either compound alone. Data are presented as mean±SEM with animal numbers equal to 8 for the groups. Statistical significance is determined by ANOVA with a Dunnett's comparison to the Example 2/Compound A combination using JMP 12.1.

4 h after the radiolabeled phosphate solution is dosed, stomach, small intestine, large intestine, and feces are collected, weighed and digested with 1N NaOH overnight at 37° C. Radioactivity in each fraction is measured by scintillation counting.

The percent dose recovered in gastrointestinal tract is defined as radioactivity recovered in stomach, small intestine, large intestine and feces compared to the amount dosed. Data is presented as mean±SEM with animal numbers equal to 8 for the groups. Statistical significance is determined by ANOVA with a Dunnett's comparison to the Example 2/Compound A combination using JMP 12.1.

Percent Radiolabeled Phosphate Dose Recovered from each Section of the GI Tract, Mean±SEM Total radioactivity recovered is greater in animals dosed with both Example 2 and Compound A (46%) than with either one alone (31% and 32%, respectively) (Table 8). Thus, the combination is more effective than either compound alone.

The percent dose recovered in gastrointestinal tract data is further analyzed by a two-way ANOVA in JMP 12.1 to test for additivity of the effects of Example 2 and Compound A on inhibiting phosphate absorption. The test of Example 2/Compound A interaction is significant (p=0.0187) indicating a synergistic relationship between the compounds at the doses tested in this study. That is, the inhibitory effect of the combination is greater than the sum of the individual compound effects.

We claim:

1. A compound of the formula:

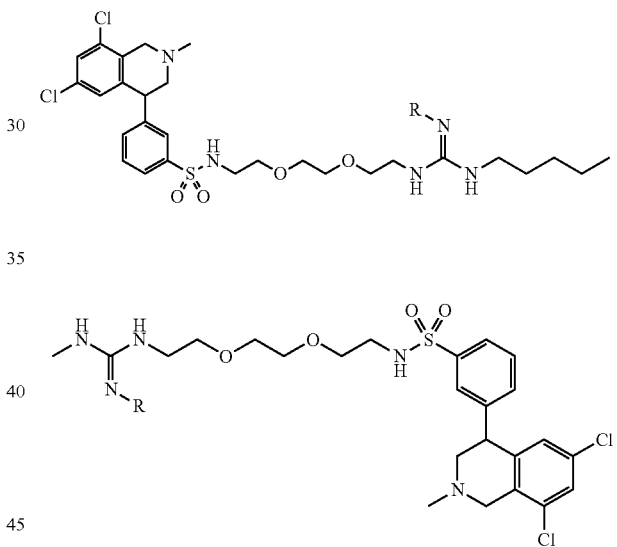

wherein both R are CN or both R are C(O)NH$_2$, or a pharmaceutically acceptable salt thereof.

2. The compound according to claim 1, wherein both R are C(O)NH$_2$, or a pharmaceutically acceptable salt thereof.

TABLE 8

The Percent Dose Recovered in Each Section of Gastrointestinal Tract.

| Treatment | Stomach | Small Intestine | Large Intestine | Feces | Total |
| --- | --- | --- | --- | --- | --- |
| Control, PVP + HEC | 5.50 ± 0.89 | 8.03 ± 0.54 | 11.83 ± 1.09 | <0.1 | 25.36 ± 1.27 |
| Example 2, 0.4 mg/kg | 3.9 ± 0.49 | 8.64 ± 0.32 | 18.16 ± 2.58 | <0.1 | 30.7 ± 2.43 |
| Compound A, 10 mg/kg | 4.86 ± 1.13 | 8.98 ± 0.48 | 18.43 ± 2.03 | <0.1 | 32.27 ± 1.38 |
| Example 2 + Compound A | 6.23 ± 0.80 | 10.76 ± 0.67 | 28.98 ± 1.93 | <0.1 | 45.96 ± 1.33 |

3. The compound according to claim 1, wherein the compound is:
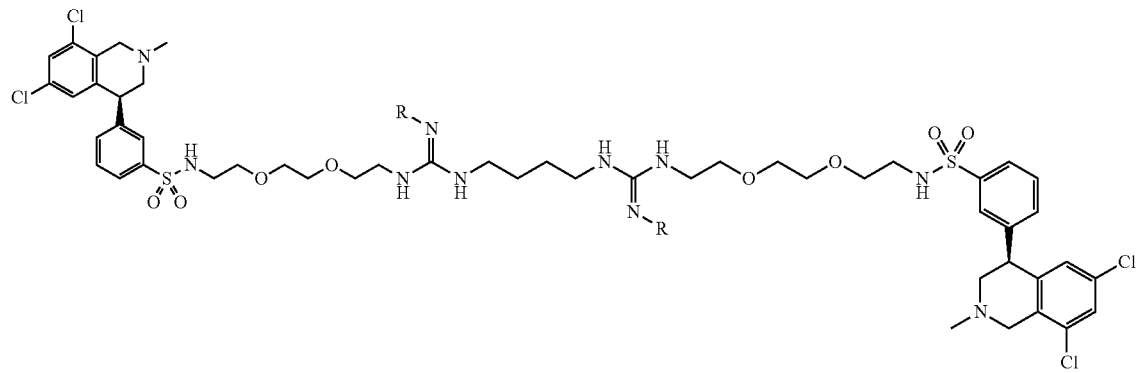
or a pharmaceutically acceptable salt thereof.
4. The compound of claim 1, wherein the compound is:
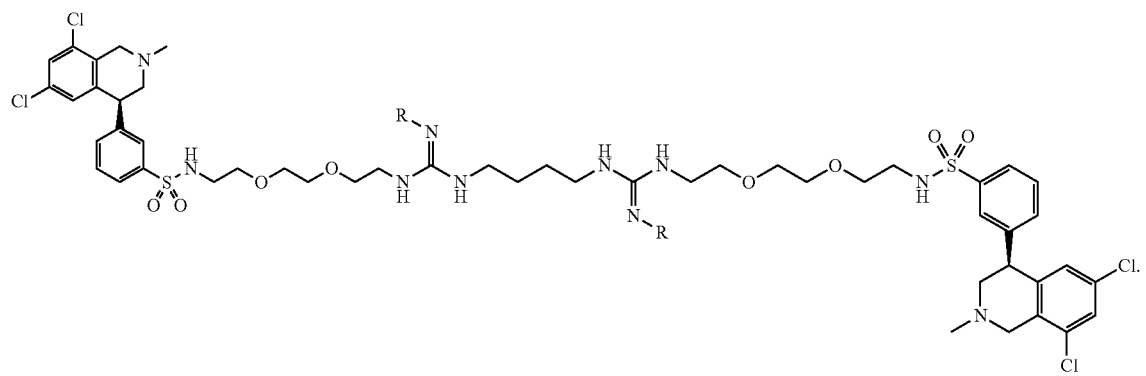
5. The compound of claim 1, wherein the compound is the dihydrochloride salt of:
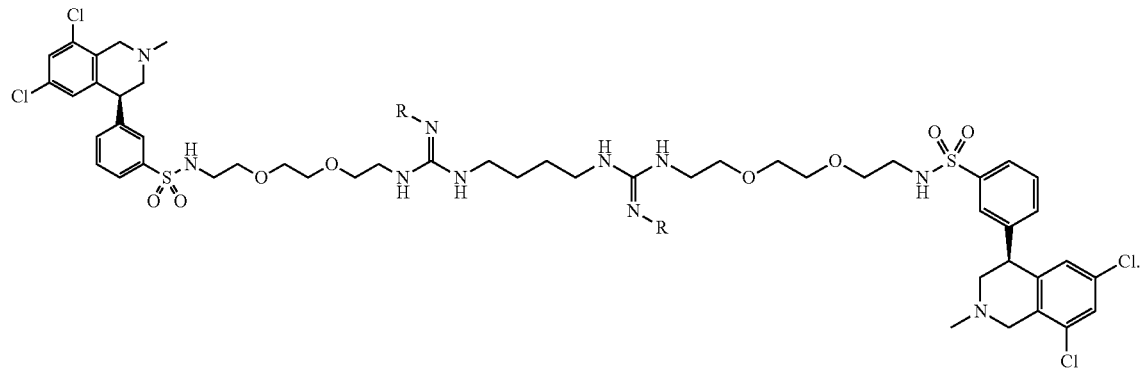

6. A compound which is:
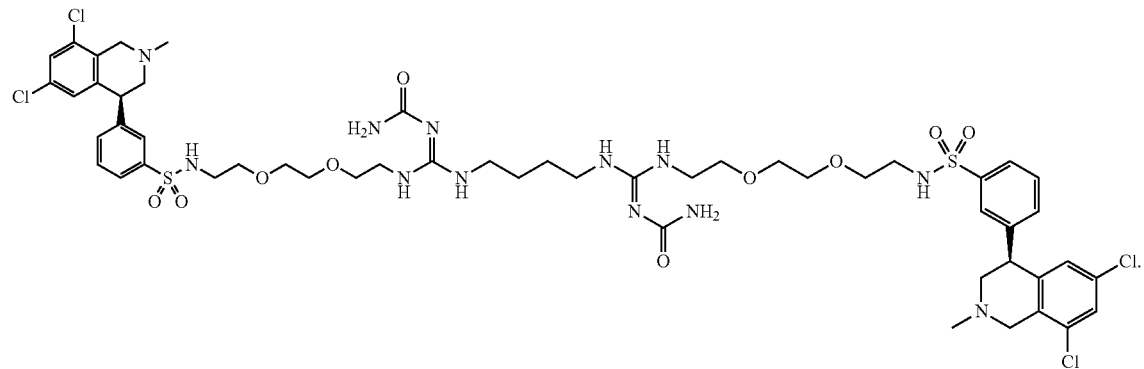 [SMILES: CN1Cc2c(Cl)cc(Cl)cc2[C@H](c2cccc(S(=O)(=O)NCCOCCOCCN/C(=N\C(N)=O)NCCCCN/C(=N/C(N)=O)NCCOCCOCCNS(=O)(=O)c3cccc([C@@H]4CN(C)Cc5c(Cl)cc(Cl)cc54)c3)c2)C1]
7. A compound which is the dihydrochloride salt of:
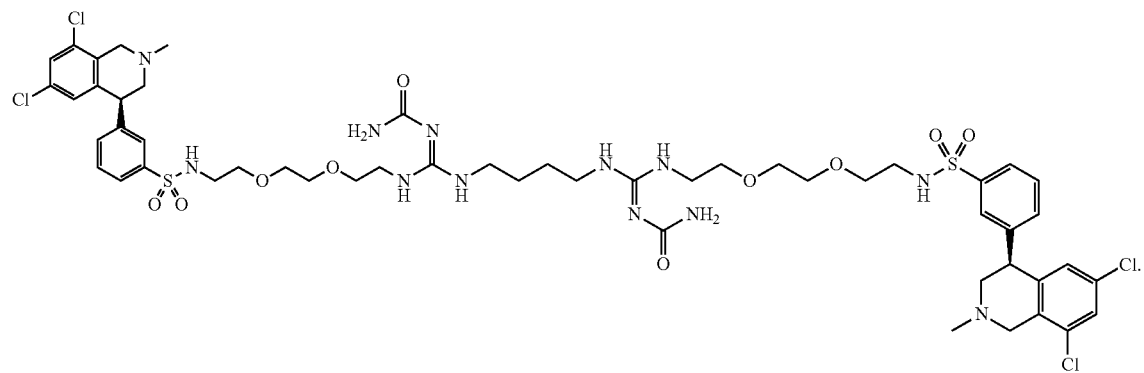 [SMILES: CN1Cc2c(Cl)cc(Cl)cc2[C@H](c2cccc(S(=O)(=O)NCCOCCOCCN/C(=N\C(N)=O)NCCCCN/C(=N/C(N)=O)NCCOCCOCCNS(=O)(=O)c3cccc([C@@H]4CN(C)Cc5c(Cl)cc(Cl)cc54)c3)c2)C1]
* * * * *